United States Patent [19]

Highgate

[11] 3,961,379

[45] June 8, 1976

[54] BIOIMPLANTABLE DEVICE FROM CROSSLINKED, SWOLLEN, HYDROPHILIC POLYMERS

[76] Inventor: Donald J. Highgate, "Brambles," Wonham Way, Gomshall, Guildford, Surrey, England

[22] Filed: July 17, 1974

[21] Appl. No.: 489,293

[30] Foreign Application Priority Data

July 18, 1973 United Kingdom............... 34188/73

[52] U.S. Cl............................................. 3/13; 3/1;
204/159.16; 260/32.8 R; 260/32.8 A;
260/32.8 N; 260/33.4 R; 260/33.4 PQ;
260/885; 351/160
[51] Int. Cl.² ...................... A61F 1/16; C08K 5/07;
C08K 5/05; C08L 31/02
[58] Field of Search............... 204/159.16; 260/885,
260/32.8 R, 33.4 R; 3/1, 13

[56] References Cited
UNITED STATES PATENTS

| | | | |
|---|---|---|---|
| 2,497,451 | 2/1950 | Haefeli............................ | 260/885 |
| 3,087,875 | 4/1963 | Graham et al................. | 204/159.16 |
| 3,826,678 | 7/1974 | Hoffman et al............... | 204/159.16 |

*Primary Examiner*—Murray Tillman
*Assistant Examiner*—Thurman K. Page
*Attorney, Agent, or Firm*—Lawrence Rosen; E. Janet Berry

[57] ABSTRACT

A method for modifying the properties of solid polymers in which a polymerizable substance is introduced into the polymer to be modified and is then polymerized. The method allows solid polymers having desirable combinations of properties not otherwise obtainable to be made and permits accurate control over the properties. The method also permits the making of solid polymer articles having different properties in different parts of their bulk and is especially valuable in making hydrophilic polymers of well controlled properties.

7 Claims, No Drawings

BIOIMPLANTABLE DEVICE FROM CROSSLINKED, SWOLLEN, HYDROPHILIC POLYMERS

An immense variety of solid polymers is known and this provides a wide range of combinations of properties that are valuable for numerous and diverse particular purposes. Solid polymers having certain combinations of properties that are desirable for some purposes cannot however be made by conventional means even by careful choice of monomers, polymerisation conditions and additives.

It has been proposed to achieve solid polymers of desirable properties by modification of other solid polymers after the latter have been made. Thus, treatment of solid polymers with modifying agents, e.g. by milling has been suggested, the product eventually being formed into a solid polymer article of modified properties. This procedure has, however, the disadvantage of involving the steps of destroying the shape of the initial solid polymer and subsequently forming the modified polymer into the desired shape. A further disadvantage of this procedure is that it is only applicable to a limited number of polymer types. Moreover, like conventional ways of making solid polymers directly, the known modification procedure has the limitation that it can only be used to form polymer articles that have substantially uniform properties throughout their bulk.

I have now found that the properties of solid polymers can be modified conveniently by a method that does not involve destruction of the original shape of the solid polymer and that enables polymers to be obtained having properties that cannot be achieved by conventional means. Furthermore, the method I have devised readily permits solid polymer articles to be obtained in which the properties vary in a controlled manner from one part of the article to another.

According to the present invention, a method for modifying the properties of solid polymers comprises swelling a piece of solid polymer in a monomer, monomer mixture or low polymer in which it is swellable and then polymerising the monomer or monomer mixture or further polymerising the low polymer.

The initial polymer must be solid but otherwise the only fundamental criterion for the polymer is that it should be swellable. Thus the initial polymer may be one having the general characteristics of typical resinous polymers or it may be of elastomeric nature; also, it may be thermoplastic or thermoset. The polymer may be a homopolymer or a copolymer of two or more monomers and it may be either crosslinked or not, although highly cross-linked polymers are not preferred.

Suitable synthetic organic polymers are commonly addition polymers, e.g. polymers of olefinically unsaturated monomers, optionally together with monomers of other types, and it is usually desirable for such polymers to have been made using a certain amount of a cross-linking agent. Typical polymers of this type are homopolymers and copolymers of monoolefinically unsaturated monomers such as alkyl and hydroxyalkyl acrylates and methacrylates for example, lower alkyl and hydroxy lower alkyl acrylates and methacrylates, e.g. methyl methacrylate and hydroxyethyl methacrylate, and acrylamide. The term "lower alkyl" signifies alkyl groups having from 1 to 4 carbon atoms. Suitable cross-linking agents for use in such polymers are, for example, diolefinically unsaturated compounds such as allyl methacrylate and ethylene glycol dimethacrylate. Other addition polymers that are suitable include rubbery polymers such as homopolymers and copolymers of conjugated dienes e.g. butadiene; a typical polymer of this type is styrene-butadiene rubber. Exemplary of synthetic organic condensation polymers to which the present method may be applied are polyamides such as nylon 6 and nylon 6,6 and aromatic polyamides.

The phenomenon of swelling solid polymers by other materials is well known and the term swelling is used because there is usually a significant increase in size of the solid polymer. The term swelling is, however, also applicable in cases where the polymer absorbs the swelling substance without significantly increasing in size.

It is characteristic of the swelling phenomenon that the swelling substance is taken up by the polymer without destruction of its physical form. Accordingly, swelling does not occur if the polymer is subjected to treatment with a substance which actually dissolves the polymer. Furthermore, many liquids not only lack the ability to dissolve the polymers but also the ability to swell them. Nonetheless, polymers are generally swellable in certain substances and for a given polymer it is generally known or predictable what substances would serve to swell it; in any event it can be determined by simple experiment whether or not a particular substance has the ability to swell a particular polymer.

Normally swelling of polymers is effected by contacting the polymer with the swelling substance in liquid form but it is possible, although usually less practical, to use the swelling substance in the vapour phase.

Monomers that I have found particularly suitable for swelling the polymer are alkylacrylates and methacrylates, e.g. methyl methacrylate and methacrylate, and amines especially tertiary amines e.g. N-vinyl-2-pyrrolidone.

The process according to the invention as described above requires that the substance used to modify the properties of the solid polymer should be one that will swell the polymer but I have devised a modified process which is not subject to this limitation. In the modified process, the polymer is first swollen with a substance which may or may not be one that can subsequently be polymerised but which is miscible with the substance by polymerisation of which it is desired to modify the polymer. The swelling substance in the swollen polymer is then exchanged with the desired modifying substance and, as before, the modifying substance polymerised.

In the modified process there is the possibility of using a wide variety of swelling substance since it is no longer a requirement that the chosen substance should be polymerisable. Examples of suitable substances are aldehydes and ketones, e.g. acetone, and alcohols such as methanol, ethanol and propanol. The exchange of the intermediate swelling substance with the desired polymerisible substance occurs by diffusion and for this reason the intermediate substance and the final polymerisible substance should be miscible.

Different swelling substance have the ability to swell a given polymer by different amounts, in any particular case there being an equilibrium content of the swelling substance in question beyond which the polymer can absorb no more swelling substance. This means that by choice of intermediate swelling substance, the initial equilibrium content of swelling substance can be controlled and thus in turn the content of the modifying polymerisible substance can be controlled. By use of mixtures of intermediate swelling substances, the ultimate content of polymerisible substance can be varied at will through a wide range.

Whether or not the polymerisible substance is introduced into the solid polymer by use of an intermediate swelling substance, the present invention enables solid polymer articles to be made having properties that can be varied in a controlled manner through the bulk of the article. Thus, if an article of the solid polymer having the polymersible substance uniformly distributed through it is subjected to a treatment which results in diffusion of the polymerisible substance from the surface, e.g. by placing the article in a vacuum oven, the content of polymerisible substance at and near the surface is reduced as compared with that in the interior of the article. Accordingly, if the polymerisible substance is then polymerised the surface parts will be modified to lesser extent than the interior. Similarly, if an intermediate swelling substance is used, the exchange of this with the polymerisible substance can be stopped before it is complete and the polymerisation then effected, the surface parts of the article thus being modified more than the interior. If desired any non-polymerisible swelling substance remaining in the article after the polymerisation can be removed e.g. by use of a vacuum oven.

The polymerisible substance can be polymerised in a variety of ways and in any particular case the most suitable way will depend on the nature of the polymerisible substance and on the initial solid polymer. Suitable polymerisation conditions for a vast variety of monomers, monomer mixtures and low polymers are known. In some cases the polymerisible substance will polymerise with little chemical interaction with the initial solid polymer molecules whilst in other cases the polymerisation will involve to a greater or lesser extent, graft polymerisation of the polymerisible substance onto the existing polymer molecules. If the polymerisible substance incorporated into the solid polymer is a low polymer then this is subjected to further polymerisation and suitable conditions for further polymerising low polymers are in general well known. If a low polymer is used this may be incorporated into the initial solid polymer by use of a solvent solution of the low polymer. For example, hydrophilic polymers that are water-swellable may be swollen by use of solutions in water of water-soluble low polymers e.g. polyacrylamide.

One method by which the desired polymerisation may be achieved is by heating, with or without assistance from chemical polymerisation initiators. Chemical initiators may be introduced into the initial solid polymer together with the polymerisible substance. If the desired polymerisation is effected by heating then the temperature used should not be so high that degradation of the solid polymer occurs and, in order to preserve the shape of the initial solid polymer article, the temperature should not be so high, in the case of a thermoplastic solid polymer, that the polymer loses its solidity.

The preferred method of effecting the polymerisation is by use of electromagnetic radiation e.g. gamma rays or by means of high energy particles e.g. electrons. The use of high energy particle radiation or electromagnetic radiation for effecting polymerisations has previously been suggested although it has been little used, but I have found the irradiation techniques are particularly suitable for effecting the desired polymerisation in processes according to the present invention. Charged particles can be obtained as accurately focused beams and this provides a way of obtaining modified solid polymer articles in which the original properties are modified in different ways in different parts of the article. Thus, for example, an article of the solid polymer having a polymerisible substance uniformly distributed through it can be subjected to the action of a focused particle beam and thus the polymerisible substance only polymerised in one part of the article. If desired the unaffected polymerisible substance can then be removed e.g. by use of a vacuum oven.

If high energy particles are used to effect the polymerisation these are preferably provided by a source giving energies in the range 1.0 KeV to 100 MeV. If ionising electromagnetic radiation is used the wavelengths (in vacuo) are preferably from $10^{-4}$ metres to $10^{-14}$ metres. Convenient sources of radiation are X-ray generators and certain radioactive isotopes.

The processes of the present invention are especially valuable for making solid polymers for very specialised purposes where particularly rigorous control over the final properties is required, as is often the case for small articles of high value. In particular the processes are of great worth for making solid polymers having carefully controlled hydrophilic properties; such polymers are needed for making bioimplantable devices e.g. contact or prosthetic lenses. Where hydrophilic end products are desired it is preferred to use an initial solid polymer having hydrophilic properties rather than to rely merely on the use of a polymerisible substance that will impart hydrophilic properties. Suitable initial hydrophilic solid polymers are copolymers of methyl methacrylate e.g. with N-vinyl-2-pyrrolidone, these preferably being cross-linked polymers in which, for example, diolefinically unsaturated crosslinking agents such as allyl methacrylate are used.

A problem with solid hydrophilic polymers has been that marked hydrophilic properties have not been obtainable simultaneously with the degree of structural strength needed for some purposes, any improvement in hydrophilic properties being accompanied by inferior strength. I have found that by use of processes according to the invention solid polymers having both excellent hydrophilic properties and good strength can readily be obtained.

Another specific field in which the invention is particularly useful is for providing solid polymers that have properties desirable in vibration damping materials. Thus, the suitability of a styrene-butadiene polymer as a vibration damping material can be greatly improved by swelling this polymer in N-vinyl-2-pyrrolidone and then polymerising the latter. This procedure results in an improvement of the elasticity and the wettability of the surface is also enhanced. Furthermore, the modified polymers have improved surface bonding characteristics.

The processes of the invention are illustrated by the following Examples.

EXAMPLE 1

In this Example the initial solid polymer was a crosslinked copolymer of N-vinyl-2-pyrrolidone (3 parts by weight) and methyl methacrylate (1 part by weight), containing 1% by weight of allyl methacrylate as crosslinking agent. This polymer is of low strength and is swellable in water; at pH7 and a temperature of 21°C the equilibrium water content of the hydrated polymer is 70% by weight.

A disk of the polymer (½ inch thick and ½ inch diameter) was swollen in 30mls of pure methanol for 48 hours at ambient temperature and pressure. The swollen polymer was then immersed in methyl methacrylate to which 0.5% by weight of allyl methacrylate had been added. After 72 hours, substantially complete exchange of the methanol in the polymer by the methyl methacrylate/allyl methacrylate had occured. The polymer was then subjected to gamma-radiation from a $Co^{60}$ source, a radiation dose of 2.5 M.rads being used.

The irradiation resulted in a solid polymer blank which retained the good wettability by water, i.e. a low contact angle, of the initial polymer but had, on swelling with water, an equilibrium water content of only 2% by weight. The modified polymer was of greatly increased strength as compared with the initial polymer. The blank could be machined into a contact lense as the wettability of the modified polymer extended throughout the entire blank rather than merely being a property of the surface of the blank.

EXAMPLE 2

Example 1 was repeated but using acetone rather than methanol to swell the solid polymer initially. It was found that the acetone swelled the polymer to a lesser extent than the methanol and that the equilibrium water content of the final modified polymer, after swelling with water, was correspondingly increased to a level above the 2% by weight figure observed in Example 1 but again markedly less than the 70% by weight figure for the unmodified polymer. The strength of the polymer was again increased as compared with the unmodified polymer but in this case to a lesser extent i.e. the final polymer was softer and more flexible.

EXAMPLE 3

Example 1 was repeated but the exchange process was not allowed to proceed to completion before the polymerisation was effected. The effects of this modification of the procedure of Example 1 were similar to those resulting from the procedure of Example 2.

EXAMPLE 4

In this Example, Example 1 was repeated with the modification that, after complete exchange had occurred, the swollen polymer was placed in a vacuum oven. After three hours the polymer was then subjected to the irradiation as in Example 1. The resulting modified polymer disk was found to have a low water uptake at its centre (2% by weight) but a higher water uptake (approaching 70% by weight) at its surface where methyl methacrylate had evaporated in the oven. By continuing the treatment in the oven for various lengths of time it was found possible to control the variation of properties throughout the disk.

EXAMPLE 5

A lightly cross-linked mthyl methacrylate polymer was swollen in N-vinyl-2-pyrrolidone containing allyl methacrylate as cross-linking agent. The swollen polymer was irradiated using a $Co^{60}$ source and this resulted in a modified polymer of improved strength having a high equilibrium water uptake. The procedure was carried out in several runs using amounts of cross-linking agent in the initial polymer varying from 1% by weight down to 0.05% by weight and using amounts of cross-linking agent with the N-vinyl-2-pyrrolidone varying from 20% by weight down to 0.02% by weight. Equilibrium water contents of the vinyl polymer, after swelling in water, as high as 90% by weight were observed.

What is claimed is:

1. A process for modifying properties of a swellable cross-linked solid polymer of at least one monomer selected from the group consisting of alkyl acrylates, alkyl methacrylates, hydroxy alkyl acrylates, hydroxy alkyl methacrylates and acrylamide comprising the steps of swelling an article of said cross-linked polymer in a mixture, in which said polymer is swellable, of at least one monomer selected from the group consisting of alkyl acrylates, alkyl methacrylates and N-vinyl-2-pyrrolidone and a cross-linking agent selected from the group consisting of allyl methacrylate and ethylene glycol dimethacrylate for the selected monomer and polymerising said mixture in the swollen polymer.

2. A process according to claim 1 in which the polymerisation is effected by subjecting the swollen polymer to irradiation.

3. A process for modifying properties of a swellable cross-linked solid polymer of at least one monomer selected from the group consisting of alkyl acrylates, alkyl methacrylates, hydroxy alkyl acrylates, hydroxy alkyl methacrylates and acrylamide comprising the steps of swelling an article of said cross-linked polymer in a substance in which said polymer is swellable and which is miscible with alkyl acrylates, alkyl methacrylates and N-vinyl-2-pyrrolidone and mixtures thereof, exchanging said substance at least partially by a polymerisable mixture comprising at least one monomer selected from the group consisting of alkyl acrylates, alkyl methacrylates and N-vinyl-2-pyrrolidone and a cross-linking agent selected from the group consisting of allyl methacrylate and ethylene glycol dimethacrylate for the selected monomer and polymerising said polymerisable mixture in the swollen polymer.

4. A process according to claim 3 in which the solid polymer is initially swollen in a substance selected from the group consisting of alcohols, aldehydes and ketones.

5. A process according to claim 3 in which the polymerisation is effected by irradiation.

6. A bioimplantable device formed of a hydrophilic solid polymer made by the process of claim 1.

7. A bioimplantable device formed of a hydrophilic solid polymer made by the process of claim 3.

* * * * *